United States Patent [19]

Harris et al.

[11] Patent Number: 5,652,271
[45] Date of Patent: Jul. 29, 1997

[54] THERAPEUTIC AGENTS

[75] Inventors: Paul John Harris; David John Heal, both of Nottingham, United Kingdom

[73] Assignee: Knoll Aktiengesellschaft, Ludwigshafen, Germany

[21] Appl. No.: 545,752

[22] PCT Filed: May 7, 1994

[86] PCT No.: PCT/EP94/01494

§ 371 Date: Dec. 22, 1995

§ 102(e) Date: Dec. 22, 1995

[87] PCT Pub. No.: WO94/26704

PCT Pub. Date: Nov. 24, 1994

[30] Foreign Application Priority Data

May 12, 1993 [GB] United Kingdom ............. 9309749

[51] Int. Cl.$^6$ ............. A61K 31/13; C07C 323/25; C07C 317/28
[52] U.S. Cl. ............. 514/646; 514/650; 514/657; 564/339; 564/391; 564/428; 564/440
[58] Field of Search ............. 564/339, 391, 564/428, 440; 514/646, 650, 657

[56] References Cited

U.S. PATENT DOCUMENTS 5,047,432  9/1991  Housley et al. ............. 514/650

FOREIGN PATENT DOCUMENTS

| 111 994 | 6/1984 | European Pat. Off. . |
| 282 206 | 9/1988 | European Pat. Off. . |
| 2098602 | 11/1982 | United Kingdom . |

Primary Examiner—Richard L. Raymond
Attorney, Agent, or Firm—Keil & Weinkauf

[57] ABSTRACT

Compounds of formula I $$R \underset{(CH_2)_n}{\overset{X-Y-S(O)_m-Z-NR_1R_2}{\bigcirc}} \qquad I$$

and pharmaceutically acceptable salts thereof in which m is 0, 1 or 2; n is 2, 3, 4 or 5; X is carbonyl or a group of formula II $$R_5 \underset{}{\overset{OH}{+}} \qquad II$$

in which $R_5$ is H or alkyl;

Y is an alkylene chain optionally substituted by one or more alkyl groups; Z is an alkylene chain containing 2 to 5 carbon atoms optionally substituted by one or more alkyl groups; R is phenyl optionally substituted by one or more halo substituents or R is naphthyl; and $R_1$ and $R_2$, which are the same or different, are H, alkyl, or arylalkyl, provided that when $R_1$ is benzyl, $R_2$ is H or methyl;

have utility in the treatment of depression, anxiety, Parkinson's disease, obesity, cognitive disorders, seizures, neurological disorders such as epilepsy, and as neuroprotective agents to protect against conditions such as stroke.

20 Claims, No Drawings

THERAPEUTIC AGENTS

This application is a 371 of PCT/EP94/01494, filed May 7, 1994.

The present invention relates to novel therapeutic agents, to processes for their preparation, to pharmaceutical compositions containing them and to their use in the treatment of depression, anxiety, Parkinson's disease, obesity, cognitive disorders, seizures, neurological disorders such as epilepsy, and as neuroprotective agents to protect against conditions such as stroke.

The present invention provides compounds of formula I

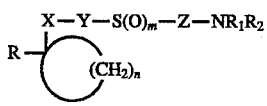

and pharmaceutically acceptable salts thereof in which
m is 0, 1 or 2;
n is 2, 3, 4 or 5;
X is carbonyl or a group of formula II

in which $R_5$ is H or an alkyl group containing 1 to 4 carbon atoms;
Y is an alkylene chain containing 1 or 2 carbon atoms optionally substituted by one or more alkyl groups containing 1 to 3 carbon atoms;
Z is an alkylene chain containing 2 to 5 carbon atoms optionally substituted by one or more alkyl groups containing 1 to 3 carbon atoms;
R is phenyl optionally substituted by one or more halo substituents which are the same or different (for example fluoro, chloro, bromo or iodo) or R is naphthyl; and
$R_1$ and $R_2$, which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl.

In preferred compounds of formula I, m is 0, 1 or 2 and n is 3 or 4.

In preferred compounds of formula I, X is carbonyl or a group of formula II in which $R_5$ is H.

In preferred compounds of formula I, Y is methylene.

In preferred compounds of formula I, Z is an alkylene chain containing 2, 3 or 4 carbon atoms optionally substituted by one or more alkyl groups containing 1 to 3 carbon atoms. In more preferred compounds of formula I, Z is an alkylene chain containing 2, 3 or 4 carbon atoms optionally substituted by one or more methyl groups.

In preferred compounds of formula I, R is phenyl substituted by one or two chloro substituents, or R is naphthyl. In more preferred compounds of formula I, R is 3-chlorophenyl, 3,4-dichlorophenyl or 2-naphthyl.

In preferred compounds of formula I, $R_1$ is an alkyl group containing 1 to 3 carbon atoms or is benzyl, and $R_2$ is an alkyl group containing 1 to 3 carbon atoms. In more preferred compounds of formula I, $R_1$ and $R_2$ are both methyl or ethyl or $R_1$ is benzyl and $R_2$ is methyl. In especially preferred compounds of formula I, $R_1$ and $R_2$ are both methyl.

A preferred group of compounds of formula I is represented by formula III

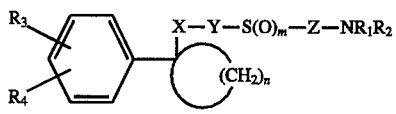

and pharmaceutically acceptable salts thereof in which m, n, X, Y, Z, $R_1$ and $R_2$ are as described above for formula I;
and $R_3$ is halo (for example fluoro, chloro, bromo or iodo), and $R_4$ is H or halo (for example fluoro, chloro, bromo or iodo), or $R_3$ and $R_4$ together with the carbon atoms to which they are attached form a fused benzene ring.

In more preferred compounds of formula III, $R_3$ is chloro and $R_4$ is H, $R_3$ and $R_4$ are both chloro or $R_3$ and $R_4$ together with the carbon atoms to which they are attached form a fused benzene ring. In especially preferred compounds of formula III, $R_3$ is chloro situated in the 3-substitution position on the phenyl ring and $R_4$ is H, $R_3$ and $R_4$ are both chloro and are situated in the 3- and 4- substitution positions on the phenyl ring respectively, or $R_3$ and $R_4$ together with the phenyl ring to which they are attached form a 2-naphthyl group.

Compounds of formula I and III may exist as salts with pharmaceutically acceptable acids. Examples of such salts include hydrochlorides, hydrobromides, sulphates, methanesulphonates, nitrates, maleares, acetates, citrates, fumarates, tartrates [eg (+)-tartrates, (−)-tartrates or mixtures thereof including racemic mixtures], succinates, benzoates and salts with amino acids such as glutamic acid. Compounds of formula I and III and their salts may exist in the form of solvates (for example hydrates).

Certain compounds of formula I and III may exist in more than one crystal form and the present invention includes each crystal form and mixtures thereof.

It will be appreciated by those skilled in the art that compounds of formula I and III may contain one or more chiral centres. When compounds of formula I and III contain one chiral centre, the compounds exist in two enantiomeric forms and the present invention includes both enantiomers and mixtures of those enantiomers. The individual enantiomers may be obtained by methods known to those skilled in the art. Such methods typically include resolution via formation of diastereoisomeric salts which may be separated, for example, by crystallisation; via formation of diastereoisomeric derivatives or complexes which may be separated, for example, by crystallisation, gas-liquid or liquid chromatography; via selective reaction of one enantiomer with an enantiomer-specific reagent, for example enzymatic esterification, oxidation or reduction; or via gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When compounds of formula I and III contain more than one chiral centre, the compounds may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of formula I and III and mixtures thereof.

Specific compounds of formula I and III are:

1-[1-(3,4-dichlorophenyl)cyclobutyl]-2-[2-(dimethylamino)ethylthio]ethanone;

1-[1-(3,4-dichlorophenyl)cyclobutyl]-2-[2-(dimethylamino)ethylsulphinyl]ethanone;

1-[1-(3,4-dichlorophenyl)cyclobutyl]-2-[2-(dimethylamino)ethylsulphonyl]ethanone;

1-[1-(3,4-dichlorophenyl)cyclobutyl]-2-[2-(diethylamino)ethylthio]ethanone;

2-[2-(N-benzyl-N-methylamino)ethylthio]-1-[1-(3,4-dichlorophenyl)cyclobutyl]ethanone;

1-[1-(3,4-dichlorophenyl)cyclobutyl]-2-[2-(dimethylamino)ethylthio]ethanol;

1-[1-(3,4-dichlorophenyl)cyclobutyl]-2-[3-(dimethylamino)propylthio]ethanone;

1-[1-(3,4-dichlorophenyl)cyclobutyl]-2-[3-(dimethylamino)propylsulphonyl]ethanone;

1-[1-(3,4-dichlorophenyl)cyclobutyl]-2-[3-(dimethylamino)propylthio]ethanol;

1-[1-(3,4-dichlorophenyl)cyclobutyl]-2-[3-(dimethylamino)-2-methylpropylthio]ethanone;

2-[2-(dimethylamino)ethylthio]-1-[1-(2-naphthyl)cyclobutyl]ethanone;

1-[1-(3-chlorophenyl)cyclobutyl]-2-[3-(dimethylamino)propylthio]ethanone;

1-[1-(3,4-dichlorophenyl)cyclobutyl]-2-[4-(dimethylamino)butylthio]ethanone;

1-[1-(3,4-dichlorophenyl)cyclobutyl]-2-[3-(dipropylamino)propylthio]ethanone;

1-[1-(3,4-dichlorophenyl)cyclobutyl]-2-[3-(dimethylamino)-2-methylpropylthio]ethanol;

1-[1-(3,4-dichlorophenyl)cyclopentyl]-2-[3-(dimethylamino)propylthio]ethanone;

and pharmaceutically acceptable salts thereof in the form of individual enantiomers, racemates, or other mixtures of enantiomers.

Specific enantiomeric forms of compounds of formula I and III are:

(−)-1-[1-(3,4-dichlorophenyl)cyclobutyl]-2-[3-(dimethylamino)propylthio]ethanol; (+)-1-[1-(3,4-dichlorophenyl) cyclobutyl]-2-[3-(dimethylamino) propylthio]ethanol;

The present invention also includes pharmaceutical compositions containing a therapeutically effective amount of a compound of formula I or III together with a pharmaceutically acceptable diluent or carrier.

As used hereinafter, the term "active compound" denotes a compound of formula I or III. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form.

Compositions for oral administration are the preferred compositions of the invention and these are the known pharmaceutical forms for such administration, for example tablets, capsules, granules, syrups, solutions and aqueous or oil suspensions. The excipients used in the preparation of these compositions are the excipients known in the pharmacist's art. Tablets may be prepared by mixing the active compound with fillers, for example calcium phosphate; disintegrating agents, for example maize starch; lubricating agents, for example magnesium stearate; binders, for example micro-crystalline cellulose or polyvinylpyrrolidone and other optional ingredients known in the art to permit tableting the mixture by known methods. The tablets may, if desired, be coated using known methods and excipients which may include enteric coating using for example hydroxypropylmethyl cellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The contents of the capsule may be formulated using known methods so as to give sustained release of the active compound. The tablets and capsules may conveniently each contain 1 to 500 mg of the active compound.

Other compositions for oral administration include, for example, aqueous suspensions containing the active compound in an aqueous medium in the presence of a non-toxic suspending agent such as sodium carboxymethyl-cellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, for example an effervescent couple formed from an acid and a carbonate or bicarbonate salt to facilitate dispersion in the liquid medium.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt of a compound of formula I or III or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I or III may be used to treat depression, anxiety, Parkinson's disease, obesity, cognitive disorders, seizures, neurological disorders such as epilepsy, and as neuroprotective agents to protect against conditions such as stroke in human beings. Whilst the precise amount of active compound administered in such treatment will depend on a number of factors, for example the age of the patient, the severity of the condition and the past medical history, and always lies within the sound discretion of the administering physician, the amount of active compound administered per day is in the range 1 to 1000 mg preferably 5 to 500 mg given in single or divided doses at one or more times during the day.

Compounds of formula I or III may be administered as a method of treating Parkinson's Disease either alone or in combination with a dopamine precursor such as levodopa and/or a dopa decarboxylase inhibitor such as carbidopa or benserazide.

In yet another aspect, the present invention provides the use of a compound of formula I or III in the manufacture of a medicament for use in the treatment of depression, anxiety, Parkinson's disease, obesity, cognitive disorders, seizures, neurological disorders such as epilepsy, and as neuroprotective agents to protect against conditions such as stroke.

Processes for the preparation of compounds of formula I will now be described. These processes form a further aspect of the present invention.

Compounds of formula I in which m is O, X is carbonyl and Y is methylene may be prepared by reaction of a compound of formula IV

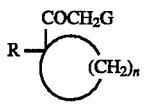    IV in which G is a leaving group, for example halo, for example chloro, bromo or iodo, with a compound of formula V

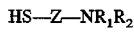    V or a salt thereof in the presence of a base, for example sodium ethoxide.

Compounds of formula IV in which G is halo may be prepared by reaction of a compound of formula VI with a halogenating agent, for example bromine.

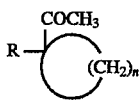    VI

Compounds of formula VI may be prepared by reaction of a compound of formula VII

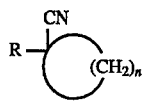    VII with an organometallic reagent, for example an organolithium compound of formula $CH_3Li$ or a Grignard reagent such as methylmagnesium iodide, followed by hydrolysis.

Compounds of formula VII in which n is 2, 3, 4 or 5 may be prepared by reaction of a compound of formula VIII

    VIII with a compound of formula IX

    IX in which n is 2, 3, 4 or 5 and Y is a leaving group, for example bromo, in the presence of a base, for example sodium hydride, sodium hydroxide or potassium hydroxide, optionally in the presence of a phase transfer catalyst, for example benzyltriethylammonium chloride.

Compounds of formula VII in which n=3 may be prepared by the method disclosed in British Patent Specification 2098602 by selection of the appropriate starting material.

Compounds of formula V may be prepared by hydrolysis, for example basic hydrolysis, of a compound of formula X or a salt thereof.

    X

Compounds of formula X may be prepared by reaction of a compound of formula XI

    XI in which A is a leaving group, for example chloro, bromo or iodo, with thiourea.

Compounds of formula XI may be prepared by reaction of a compound of formula XII

    XII with a halogenating agent, for example thionyl chloride.

Compounds of formula I in which X is a group of formula II may be prepared by reduction of a compound of formula I in which X is carbonyl, for example with sodium borohydride to give compounds of formula I in which $R_5$ is H, or by reaction of a compound of formula I in which X is carbonyl with an organometallic reagent, for example an organolithium compound of formula $R_5Li$ in which $R_5$ is alkyl to give compounds in which $R_5$ is alkyl.

Compounds of formula I in which m is 1 may be prepared by oxidising a compound of formula I in which m is 0 with an oxidising agent, for example magnesium monoperoxyphthalate.

Compounds of formula I in which m is 2 may be prepared by oxidising a compound of formula I in which m is 0 or 1 with an oxidising agent, for example potassium permanganate.

Compounds of formula I in which m is 0, X is carbonyl and Y is ethylene may be prepared by the addition reaction of a compound of formula V with a compound of formula XIII

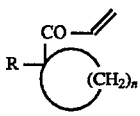

XIII

Compounds of formula XIII may be prepared by the reaction of a compound of formula XIV

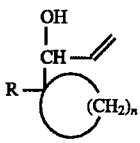

XIV with an oxidising agent, for example manganese dioxide.

Compounds of formula XIV may be prepared by the reaction of a compound of formula XV

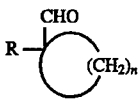

XV with an organometallic reagent, for example a Grignard reagent of formula $CH_2=CHMgCl$.

Compounds of formula XV may be prepared by reduction of a compound of formula VII with a suitable reducing agent, for example diisobutylaluminium hydride, followed by hydrolysis.

Compounds of formula III may be prepared in a similar manner to that described for compounds of formula I.

The therapeutic activity of the compounds of formula I or III has been indicated by assessing the ability of the compounds to prevent the ptosis (eye closure) induced by reserpine in the following manner. Male rats of the Charles River CD strain weighing between 140 and 180 g were randomly separated into five rats in each cage and supplied with food and water ad libitum. Eighteen hours prior to initiation of the test four of the five rats were marked with a pen such that each rat was individually identifiable; food was then withdrawn. The following morning, two hours before the test, the rats were weighed and a semi-randomised code was used to allocate treatments to rats. The test commenced by orally administering either:

a) the test compound in solution in deionised water at a dose volume of 10 ml/kg of body weight, followed by immediate intravenous injection of 1 ml/kg of body weight of reserpine (0.75 mg/kg) in solution in deionised water containing 238 mM citric acid, 1.02% v/v Tween 80 and 0.2% v/v benzyl alcohol (treated group);

b) deionised water at a dose volume of 10 ml/kg of body weight, followed by immediate intravenous injection of 1 ml/kg of body weight of reserpine (0.75 mg/kg) in solution in deionised water containing 238 mM citric acid, 1.02% v/v Tween 80 and 0.2% v/v benzyl alcohol (positive control group); or c) deionised water at a dose volume of 10 ml/kg of body weight, followed by immediate intravenous injection of 1 ml/kg of body weight of deionised water containing 238 mM citric acid, 1.02% v/v Tween 80 and 0.2% v/v benzyl alcohol (negative control group).

Three hours later rats were individually placed in clear perspex boxes (42×22×22 cm) and observed by a person who was unaware of the treatment received by each animal. The degree of ptosis was scored 45 seconds and 75 seconds later using the following observer rating system: 0=eye fully open, 1=eye ¼closed, 2=eye ½closed, 3=eye ¾closed, 4=eye fully closed. A mean ptosis score was then calculated for all identically treated rats usually comprising a group of eight rats. The mean ptosis score of the negative control group was then subtracted from the mean ptosis score of the positive control group to give the ptosis score induced by reserpine in the absence of the test compound. The mean prosis score for each group of treated rats was determined at more than one dose of test compound to enable a value for the dose ($ED_{50}$) which causes a 50% prevention of the reserpine-induced ptosis to be obtained. Examples of compounds which gave $ED_{50}$ values of 30 mg/kg or less are given in Table 1. It is widely understoodby those skilled in the art that this test is indicative of compounds having antidepressant activity in humans.

The ability of compounds of formula I or III to interact with dopamine reuptake sites has been demonstrated by the following test which determines the ability of compounds to inhibit dopamine uptake in vitro.

Striatal tissue from the brains of male Charles River rats weighing 150–250 g was homogenised in ice-cold 0.32M sucrose (1:10 w/v) using a motor driven teflon pestle (difference in diameter between mortar and pestle 0.5 mm). Nuclei and cell debris were removed by centrifugation at 1,500 g at 4° C. for 10 minutes. The pellet (P1) was discarded and the supernatant centrifuged at 18,000 g at 4° C. for 10 minutes. The crude synaptosomal pellet (P2) was resuspended in Krebs-Henseleit buffer (equivalent to 4.2 mg wet weight of tissue/ml).

Crude synaptosomes were incubated in a shaking water bath at 37° C. for 15 minutes. Aliquots (150 µl; equivalent to 0.625 mg wet weight of tissue/tube) were then added to tubes containing 275 µl of Krebs-Henseleit buffer and 50 µl of Krebs-Henseleit buffer (total uptake) or 50 µl of test compound (10 concentrations ranging from 10-11-10-4M) or 50 µl of GBR 12909 (10-5M; non-specific uptake). Uptake was initiated by the addition of 25 µl of freshly prepared [3H]dopamine (2.5 nM), followed by vortexing and was continued for 5 minutes at 37° C. in the shaking water bath.

Uptake was terminated by filtration under vacuum through Skatron 11735 filters using a Skatron cell harvester. Filters were than washed with 8 ml ice-cold saline. The scored filter paper discs were punched into vials, scintillation fluid added and radioactivity determinedby liquid scintillation counting.

The percentage inhibition of specific uptake of the tritiated ligand was calculated for each concentration of test compound. Inhibition curves were then produced. The concentration of compounds which gave 50% inhibition of specific uptake (IC50) was obtained from the curve. The inhibition constant (Ki) was then calculated using the formula $$Ki = \frac{IC50}{1+([L]/Km)}$$

in which [L] is the concentration of tritiated ligand used and Km is the affinity of the uptake site for the ligand. The Ki values for compounds for formula I and III are given in Table 1 as the means ± sem of three independent determinations.

TABLE 1

| Example No | ED$_{50}$ (mg/kg) | Ki (nM) |
| --- | --- | --- |
| 1 | 8.5 | NT |
| 2 | 7.7 | NT |
| 3 | 5.9 | NT |
| 4 | 9.7 | NT |
| 5 | 16.4 | NT |
| 6 | 5.7 | NT |
| 7 | 4.2 | 5.0 ± 0.5 |
| 8 | 3.4 | 13.4 ± 0.1 |
| 9 | 4.8 | 7.3 ± 1.6 |
| 10 | 8.7 | 7.2 ± 1.0 |
| 11 | 24.1 | NT |
| 12 | 23.4 | NT |
| 13 | 5.9 | 6.5 ± 1.0 |
| 14 | 7.3 | 13.4 ± 2.1 |
| 15 | 4.0 | 3.7 ± 0.4 |
| 16 | 2.2 | NT |
| 17 | 2.5 | NT |
| 18 | 4.9 | 4.2 ± 0.4 |
| 19 | 6.9 | 6.9 ± 0.6 |
| 20 | 3.7 | 4.4 ± 0.2 |

NT = not tested

The invention is illustrated by the following Examples which are given by way of example only. The final product of each of these Examples was characterised by one or more of the following procedures: gas-liquid or high performance liquid chromatography; elemental analysis, nuclear magnetic resonance spectroscopy and infrared spectroscopy.

EXAMPLE 1

Methylmagnesium iodide was prepared under nitrogen by dropwise addition of a solution of methyl iodide (93.8 g) in ether (100 ml), to a stirred suspension of magnesium turnings (15.9 g) in ether (100 ml) initially at ambient temperature then, when the exothermic reaction commenced, at reflux temperature. After the addition was complete the mixture was stirred for 30 minutes then a solution of 1-(3,4-dichlorophenyl)-cyclobutanecarbonitrile (100 g) in ether (80 ml) was added dropwise at ambient temperature. The resulting suspension was stirred and heated under reflux for 3 hours then stirred at ambient temperature under nitrogen for 16 hours. The resulting solid was collected by filtration, washed well with ether, then added in portions to an ice-cold mixture of water (400 ml) and concentrated hydrochloric acid (250 ml). The resulting mixture was heated at 95° C. for 1 hour with occasional stirring then cooled to ambient temperature. The product was extracted into ether (6×150 ml), the extracts were dried over magnesium sulphate and the solvent removed in vacuo to give an oil (105 g) which was distilled to give 1-[1-(3,4-dichlorophenyl)-cyclobutyl]ethanone (89.6 g), bp 116°–118° C./0.13 mbar.

A solution of bromine (18 ml) in chloroform (80 ml) was added dropwise at 10°–15° C. over 1.5 hours to a stirred solution of the above 1-[1-(3,4-dichlorophenyl)-cyclobutyl] ethanone (89.6 g) in a mixture of methanol (120 ml) and chloroform (20 ml). When the addition was complete, the mixture was stirred at ambient temperature for 1 hour, then poured onto an excess of ice-water. The aqueous layer was separated and the product extracted into dichloromethane (2×150 ml). The combined organic solutions were washed with saturated aqueous sodium hydrogen carbonate solution (2×200 ml) then with water, dried over calcium chloride and the solvent removed in vacuo to yield an oil. The oil was distilled to give 2-bromo-1-[1-(3,4-dichlorophenyl)-cyclobutyl]ethanone (88.31 g), b.p. 148°–154° C./0.66 mbar.

A solution of sodium ethoxide [prepared from sodium (0.69 g) and ethanol (60 ml)] was added to a stirred suspension of 2-(dimethylamino)ethanethiol hydrochloride (2.12 g) in ethanol (30 ml) and the mixture was stirred at ambient temperature for 1 hour. A solution of 2-bromo-1-[1-(3,4-dichlorophenyl)cyclobutyl]ethanone (4.8 g, prepared as described above) in ethanol (30 ml) was added in one portion, and the mixture was stirred at ambient temperature for a further 2 hours. The mixture was then stirred at 50° C. for 1 hour, and the solvent removed in vacuo. The residue was diluted with water (30 ml) and the product was extracted into ether (2×50 ml). The extracts were dried over magnesium sulphate, and the solvent removed in vacuo to give an oil (5.1 g).

The above oil was dissolved in ether and the solution saturated with hydrogen chloride. The solvent was removed in vacuo to give an oil (5.1 g) which was purified via flash chromatography over silica using dichloromethane followed by a 1:1 mixture of ethyl acetate and methanol as eluants. Appropriate fractions were combined and the solvents removed in vacuo to give 1-[1-(3,4-dichlorophenyl) cyclobutyl]-2-[2-(dimethyl-amino)ethylthio]ethanone hydrochloride as an oil (2.9 g).

EXAMPLE 2

1-[1-(3,4-Dichlorophenyl)cyclobutyl]-2-[2-(dimethylamino)ethylthio]ethanone (1.7 g, prepared by basification of the hydrochloride salt obtained in a similar manner to that described in Example 1) was dissolved in ethanol (10 ml) and a solution of magnesium monoperoxyphthalate hexahydrate (1.6 g, 87% purity) in water (75 ml) was added. Further ethanol (20 ml) was added and the mixture was stirred at ambient temperature for 1 hour.

The solvent was removed in vacuo, the residue diluted with water and the product extracted into ethyl acetate. The extract was dried over magnesium sulphate and the solvent removed in vacuo to give an oil (1.8 g).

The above oil was dissolved in ethanol and the solution saturated with hydrogen chloride to give a solid which was collected by filtration, and crystallised from ethanol to give 1-[1-(3,4-dichlorophenyl)cyclobutyl]-2-[2-(dimethylamino) ethylsulphinyl]ethanone hydrochloride as a white solid (0.5 g), m.p. 184°–185° C.

EXAMPLE 3

A solution of potassium permanganate (1.2 g) in water (40 ml) was added to a solution of 1-[1-(3,4-dichlorophenyl) cyclobutyl]-2-[2-(dimethylamino)ethylthio]ethanone (1.4 g, prepared by basification of the hydrochloride salt obtained in a similar manner to that described in Example 1), tetra-n-butylammonium bromide (0.1 g) and acetic acid (10 ml) in toluene (30 ml), and the mixture was stirred at ambient temperature for 22 hours. Saturated aqueous sodium hydrogen sulphite solution was added to the mixture until the purple colour disappeared and the resulting clear solution was neutralised by the addition of solid potassium carbonate. The product was extracted into toluene, the extracts were dried over magnesium sulphate, and the solvent removed in vacuo to give an oil (1.7 g)

The above oil was dissolved in ethanol and an excess of ethereal hydrogen chloride solution was added. The resulting solution was evaporated to give an oil which was triturated with dichloromethane to give 1-[1-(3,4-dichlorophenyl)cyclobutyl]-2-[2-(dimethylamino) ethylsulphonyl]ethanone hydrochloride as a white solid (0.1 g), m.p. 208°–210° C.

EXAMPLE 4

A solution of sodium ethoxide [prepared from sodium (0.5 g) and ethanol (40 ml)] was added to a solution of 2-(diethylamino)ethanethiol hydrochloride (1.7 g) in ethanol (30 ml) and the mixture was stirred at ambient temperature for 1 hour. A solution of 2-bromo-1-[1-(3,4-dichlorophenyl) cyclobutyl]ethanone (3.2 g, prepared in a similar manner to that described in Example 1) in ethanol (30 ml) was added in one portion and the mixture was stirred at ambient temperature for 1.5 hours. The solvent was removed in vacuo and the residue diluted with water (25 ml). The product was extracted into ether (2×50 ml), the extracts were dried over magnesium sulphate and the solvent removed in vacuo to give an oil (3.5 g).

The above oil was purified via flash chromatography over silica using, sequentially, a 1:1 mixture of dichloromethane and ethyl acetate, ethyl acetate, and a 9:1 mixture of ethyl acetate and methanol as eluants. Appropriate fractions were combined, and the solvents removed in vacuo to give an oil. The oil was dissolved in ether (15 ml) and the solution was saturated with hydrogen chloride. A cream solid precipitated and was collected by filtration, washed with a little ether, and dried in vacuo to yield 1-[1-(3,4-dichlorophenyl)cyclobutyl]-2-[2-(diethylamino)ethylthio]ethanone hydrochloride (1.6 g), m.p. 109°–110° C.

EXAMPLE 5

A solution of sodium ethoxide [prepared from sodium (0.2 g) and ethanol (25 ml)] was added to a solution of 2-(N-benzyl-N-methylamino)ethanethiol (1.8 g) in ethanol (20 ml), and the mixture was stirred at ambient temperature for 1 hour.

A solution of 2-bromo-1-[1-(3,4-dichlorophenyl)- cyclobutyl]ethanone (3.2 g, prepared in a similar manner to that described in Example 1) in ethanol (20 ml) was added, and the mixture was stirred at ambient temperature for 3 hours. The solvent was removed in vacuo and the residue was diluted with water (15 ml). The product was extracted into dichloromethane, the extracts dried over calcium chloride and the solvent removed in vacuo to give an oil. The oil was dissolved in ethanol and the solution saturated with hydrogen chloride to give a solid, which was collected by filtration, washed with a little ethanol, and dried in vacuo to yield 2-[2-(N-benzyl-N-methylamino)ethylthio]-1-[1-( 3,4-dichlorophenyl)cyclobutyl]ethanone hydrochloride (1.2 g), m.p. 159°–163° C.

EXAMPLE 6

A mixture of 1-[1-(3,4-dichlorophenyl)cyclobutyl]-2-[2-(dimethylamino)ethylthio]ethanone (2.0 g, prepared by basification of the hydrochloride salt obtained in a similar manner to that described in Example 1) and sodium borohydride (2.2 g) in propan-2-ol (80 ml) was stirred at ambient temperature for 16 hours.

The resulting suspension was cautiously diluted with acetone (15 ml), followed by an excess of saturated aqueous ammonium chloride solution. The resulting mixture was concentrated in vacuo, the residue was diluted with water and the product extracted into ether. The extracts were dried over magnesium sulphate and the solvent removed in vacuo to give an oil.

The oil was dissolved in ethyl acetate and the solution saturated with hydrogen chloride. The solution was diluted with ether. A gum formed and the supernatant liquor was removed by decantation and allowed to concentrate at ambient temperature. An oil was deposited and was separated by decantation of the liquor. The oil was dissolved in methanol and the solvent removed by evaporation to give 1-[1-(3,4-dichlorophenyl)cyclobutyl]-2-[2-(dimethylamino)ethylthio]ethanol hydrochloride as a colourless oil (1.55 g).

EXAMPLE 7

A mixture of 1-chloro-3-(dimethylamino)propane hydrochloride (200 g), thiourea (98.1 g) and ethanol (1l) was stirred and heated under reflux for 25 hours. The solution was cooled to ambient temperature and ethyl acetate added until permanent opalescence was obtained. The mixture was stored at 4° C. overnight then filtered to give S-[3-(dimethylamino)propyl]isothiourea dihydrochloride as a colourless solid. (283 g), m.p. 155°–159° C.

S-[3-(Dimethylamino)propyl]isothiourea dihydrochloride (283 g) was dissolved in water (340 ml) and the solution covered with a layer of ether. The mixture was cooled in ice and 25M aqueous sodium hydroxide solution (97 ml) was added dropwise. After the addition the mixture was stirred and heated under reflux for 2 hours. The solution was cooled to ambient temperature and the product extracted into ether. The extract was dried over magnesium sulphate and the solvent removed in vacuo to give a clear oil (70.6 g), a sample of which (35 g) was dissolved in ether. The resulting solution was saturated with hydrogen chloride to give a colourless solid which was collected by filtration, washed with ether, and dried in vacuo to give 3-(dimethylamino) propanethiol hydrochloride (21.2 g), m.p. 103°–107° C.

A solution of sodium ethoxide [prepared from sodium (1.0 g) and ethanol (60 ml)] was added to a suspension of 3-(dimethylamino)propanethiol hydrochloride (3.5 g) in ethanol (50 ml), and the mixture was stirred at ambient temperature for 1 hour. A solution of 2-bromo-1-[1-(3,4-dichlorophenyl)cyclobutyl]ethanone (9.35 g, prepared in a similar manner to that described in Example 1) in ethanol (30 ml) was added in one portion, and the mixture was stirred at ambient temperature for 25 hours.

The solvent was removed in vacuo to give a solid residue. Water (30 ml) was added. The product was extracted into ethyl acetate, the extract was dried over magnesium sulphate and the solvent removed in vacuo to give an oil (10.5 g). The oil was dissolved in ethyl acetate and the solution was saturated with hydrogen chloride. The solvent was removed in vacuo to give an oil (9.1 g), which was purified via flash chromatography over silica using a 1:1 mixture of ethyl acetate and methanol as eluant. Appropriate fractions were combined, and the solvents removed in vacuo to leave an oil (5 g).

The above oil was rebasified by addition to an excess of 5M aqueous sodium hydroxide solution, and the free base was extracted into ether (2×25 ml). The extracts were washed with water, dried over magnesium sulphate and the solvent removed in vacuo to give an oil. The oil was dissolved in ether and saturated with hydrogen chloride to give a white solid which was collected by filtration, washed with a little ether, and dried in vacuo to yield 1-[1-(3,4-dichlorophenyl)-cyclobutyl]-2-[3-(dimethylamino) propylthio]ethanone hydrochloride (1.6 g), m.p. 115°–118° C.

EXAMPLE 8

A solution of potassium permanganate (3.1 g) in water (95 ml) was added to a mixture of 1-[1-(3,4-dichlorophenyl) cyclobutyl]-2-[3-(dimethylamino)-propylthio]ethanone (3.4 g, prepared by basification of the hydrochloride salt obtained in a similar manner to that described in Example 7), tetra-n-butylammonium bromide (0.3 g), acetic acid (25 ml) and toluene (80 ml), and the mixture was stirred at ambient temperature for 72 hours. Saturated sodium metabisulphite solution (~100 ml) was added to the resulting brown solution until the colour changed to orange, then the mixture was neutralised by the addition of solid potassium carbonate.

The product was extracted into ethyl acetate (3×300 ml) (filtration was required for the removal of interfacial solids), the extracts were combined, dried over magnesium sulphate and the solvent removed in vacuo to give a brown oil (3.7 g).

The oil was purified via flash chromatography over silica using a 4:1 mixture of toluene and triethylamine followed by a 1:1 mixture of toluene and triethylamine as eluants. Appropriate fractions were combined and the solvents removed in vacuo to give a brown oil which crystallised on standing (0.7 g).

The solid was dissolved in a mixture of hot diethyl ether (50 ml) and ethyl acetate (8 ml) and the resulting solution was filtered, cooled and saturated with hydrogen chloride. The resulting solid was collected by filtration, dried in vacuo at 40° C. for 24 hours then ground and redried in vacuo at 40° C. for a further 24 hours to give 1-[1-(3,4-dichlorophenyl)cyclobutyl]-2-[3-(dimethylamino)propylsulphonyl]ethanone hydrochloride as a white solid (0.4 g), m.p. 168°–176° C.

EXAMPLE 9

A solution of 1-[1-(3,4-dichlorophenyl)cyclobutyl]-2-[3-(dimethylamino)propylthio]ethanone (4.6 g, prepared by basification of the hydrochloride salt obtained in a similar manner to that described in Example 7) in propan-2-ol (75 ml) was added dropwise to a stirred suspension of sodium borohydride (4.8 g) in propan-2-ol (100 ml) at ambient temperature under a nitrogen atmosphere, and the mixture was stirred at ambient temperature for 93 hours.

The resulting suspension was cautiously diluted with acetone (33 ml) followed by saturated aqueous ammonium chloride solution (100 ml).

The resulting neutral mixture was concentrated in vacuo, the residue was diluted with water (100 ml) and the product extracted into ether (3×200 ml). The extracts were combined, dried over magnesium sulphate and the solvent removed in vacuo to give a yellow oil (4 g).

The product was purified via flash chromatography over silica using a 9:1 mixture of dichloromethane and industrial methylated spirits (IMS) followed by a 4:1, then 1:1 mixture of dichloromethane and IMS as eluants. Appropriate fractions were combined and the solvents removed in vacuo to yield 1-[1-(3,4-dichlorophenyl)cyclobutyl]-2-[3-(dimethylamino)propyl-thio]ethanol as a pale green oil (1.44 g).

EXAMPLE 10

A mixture of 1-chloro-3-(dimethylamino)-2-methylpropane hydrochloride (200 g), thiourea (97.3 g) and ethanol (950 ml) was stirred and heated under reflux for 72 hours. The solution was allowed to cool and the solvent was removed in vacuo. The residue was dissolved in a small volume of ethanol and ether was added until the first permanent opalescence was observed. The mixture was stored at 4° C. for 16 hours. The solvent was removed in vacuo to afford a waxy/oily solid which was dried in vacuo over calcium chloride for 48 hours, then triturated with propan-2-ol. The resulting solid was collected by filtration, washed with propan-2-ol, and dried in vacuo to give S-[3-(dimethylamino)-2-methylpropyl]isothiourea dihydrochloride as a pale brown solid (90 g).

A solution of sodium hydroxide (19.3 g) in water (20 ml) was added dropwise at 0° C. to a stirred solution of S-[3-(dimethylamino)-2-methylpropyl]isothiourea dihydrochloride (60 g) in water (100 ml). The stirred mixture was heated at 95° C. for 2 hours and allowed to cool. The product was extracted into ether (4×70 ml), the combined extracts dried over sodium sulphate and the solvent removed in vacuo. The residual oil was dissolved in ether and the solution saturated with hydrogen chloride. The resulting solid was collected by filtration, washed with ether, and dried in vacuo over phosphorus pentoxide for 24 hours to give 3-(dimethylamino)-2-methylpropanethiol hydrochloride as a white solid (30 g).

A solution of sodium ethoxide [prepared from sodium (3 g) in ethanol (300 ml)] was added to a suspension of 3-(dimethylamino)-2-methylpropanethiol hydrochloride (10.3 g) in ethanol (150 ml) under nitrogen at ambient temperature, then the mixture was stirred at ambient temperature for 1 hour. A solution of 2-bromo-1-[1-(3,4-dichlorophenyl)cyclobutyl]ethanone (20.4 g, prepared in a similar manner to that described in Example 1) in ethanol (130 ml) was added and the mixture was stirred at ambient temperature for 24 hours. The solvent was removed in vacuo and the residue was diluted with water (150 ml). The product was extracted into dichloromethane (4×100 ml), the combined extracts were dried over sodium sulphate and the solvent was removed in vacuo. The residue was dissolved in ether and the solution saturated with hydrogen chloride. The resulting solid was collected by filtration, washed with ether, and dried in vacuo for 24 hours. The solid crystallised from a 2:1 mixture of ethyl acetate and propan-2-ol to give 1-[1-(3,4-dichlorophenyl)]-2-[3-(dimethylamino)-2-methylpropylthio]ethanone hydrochloride as a white solid, (0.55 g), m.p. 136°–137° C.

EXAMPLE 11

Methylmagnesium iodide was prepared under nitrogen by dropwise addition of a solution of methyl iodide (48.3 g) in ether (72 ml) to a stirred suspension of magnesium turnings (8.2 g) in ether (60 ml) initially at ambient temperature, then when the exothermic reaction commenced, at reflux temperature. After the addition the mixture was stirred at ambient temperature for 30 minutes and a solution of 1-(2-naphthyl)cyclobutane-carbonitrile (48.2 g) in toluene (100 ml) was added dropwise at ambient temperature. The resulting mixture was stirred at ambient temperature for 16 hours.

The resulting solid was collected by filtration, washed with ether and added in portions to a mixture of concentrated hydrochloric acid (125 ml) and water (200 ml). The resulting mixture was heated at ~95° C. for 10 minutes, cooled and the product extracted into toluene (3×200 ml). The extracts were washed with water (200 ml), dried over magnesium sulphate and the solvent removed in vacuo to give an oil (45 g). The oil was triturated with petroleum ether (b.p. 40°–60° C.) to give a solid which was collected by filtration and dried in vacuo to yield 1-[1-(2-naphthyl)cyclobutyl]ethanone (35 g).

A solution of bromine (4.3 ml) in chloroform (20 ml) was added dropwise over 30 minutes at 10°–15° C. to a stirred solution of 1-[1-(2-naphthyl)cyclobutyl]-ethanone (20 g) in a mixture of methanol (20 ml) and chloroform (30 ml). The mixture was then stirred at ambient temperature for 1.5 hours, poured onto ice-water (300 ml) and the product extracted into dichloromethane (3×150 ml). The extracts were washed with saturated aqueous sodium hydrogen carbonate solution, then water, dried over calcium chloride and the solvent removed in vacuo to give 2-bromo-1-[1-(2-naphthyl)cyclobutyl]-ethanone as an oil (24.0 g).

A solution of sodium ethoxide [prepared from sodium (6.5 g) and ethanol (100 ml)] was added to a suspension of 2-(dimethylamino)ethanethiol hydrochloride (6.4 g) in ethanol (10 ml), and the mixture stirred at ambient temperature for 1 hour. A solution of 2-bromo-1-[1-(2-naphthyl)cyclobutyl]ethanone (19.5 g, prepared as described above) in ethanol (50 ml) was added and the mixture was stirred at ambient temperature for 18 hours. The solvent was removed in vacuo, and the residue was diluted with water (200 ml). The product was extracted into ethyl acetate (2×200 ml), and the extracts were dried over magnesium sulphate and the solvent removed in vacuo to give an oil (11.0 g). The oil was dissolved in ethyl acetate and the solution saturated with hydrogen chloride. The solvent was removed in vacuo to give an oil (8.5 g) which was triturated with a mixture of propan-2-ol, ether and ethyl acetate to give a solid. The solid was collected by filtration and dried in vacuo to give 2-[2-(dimethylamino)ethylthio]-1-[1-(2-naphthyl)cyclobutyl]ethanone hydrochloride as a cream solid (1.7 g), m.p. 95°–102° C.

EXAMPLE 12

Methylmagnesium iodide (138 ml of 3M solution in ether) was added dropwise to a stirred solution of 1-(3-chlorophenyl)cyclobutanecarbonitrile (53 g) in ether (100 ml) under nitrogen at 0° C. The mixture was stirred at ambient temperature for 24 hours. The resulting solid was collected by filtration, washed well with ether, then added in portions to an ice-cold mixture of water (200 ml) and concentrated hydrochloric acid (125 ml). The resulting yellow suspension was heated at 95° C. for 1 hour with occasional stirring, and then cooled to ambient temperature. The product was extracted into ether (5×100 ml) and the combined extracts washed with water (2×100 ml), dried over magnesium sulphate and the solvent removed in vacuo to give an oil which was distilled to give 1-[1-(3-chlorophenyl)cyclobutyl]ethanone (47.5 g), b.p. 108°–109° C./2 mbar.

A solution of bromine (9.9 ml) in dichloromethane (50 ml) was added dropwise at 10°–15° C. over 3 hours to a stirred solution of 1-[1-(3-chlorophenyl)cyclobutyl]-ethanone (38 g) in a mixture of methanol (75 ml) and dichloromethane (15 ml). When the addition was complete, the mixture was stirred at ambient temperature for 2.5 hours, then poured onto an excess of ice-water. The aqueous layer was separated and the product extracted into dichloromethane (3×90 ml). The combined organic solutions were washed with saturated aqueous sodium hydrogen carbonate solution (2×100 ml) and water (100 ml), dried over calcium chloride and the solvent removed in vacuo to leave 2-bromo-1-[1-(3-chlorophenyl)cyclobutyl]ethanone as an oil (47 g).

A solution of sodium ethoxide [prepared from sodium (5.3 g) and ethanol (500 ml)] was added to a stirred suspension of 3-(dimethylamino)propanethiol hydrochloride (16.2 g, prepared in a similar manner to that described in Example 7) in ethanol (250 ml) under nitrogen and the mixture was stirred at ambient temperature for 1 hour. A solution of 2-bromo-1-[1-(3-chlorophenyl)cyclobutyl] ethanone (30 g) in ethanol (130 ml) was added in one portion, and the mixture was stirred at ambient temperature for a further 24 hours. The solvent was removed in vacuo, and the residue was diluted with water (200 ml). The product was extracted into dichloromethane (4×100 ml). The combined extracts were dried over magnesium sulphate and the solvent removed in vacuo to afford a red/brown oil (31 g).

A sample (8 g) of the above oil was dissolved in ether and the solution saturated with hydrogen chloride. The solvent was removed in vacuo and the residue triturated with ether. The resulting solid was collected by filtration and crystallised from propan-2-ol/ether to give 1-[1-(3-chlorophenyl) cyclobutyl]-2-[3-(dimethylamino)propylthio]ethanone hydrochloride as a white solid (1.7 g), m.p. 66°–68° C.

EXAMPLE 13

4-(Dimethylamino)butanol (88.5g) was added dropwise at 0° C. over 2 hours to stirred thionyl chloride (93.4 g) then the mixture was stirred at ambient temperature for 1 hour and poured into ethanol (500 ml). The stirred solution was heated under reflux for 10 minutes, then the solvent was removed in vacuo. The solid residue crystallised from ethanol as a white solid which was collected by filtration, washed with ethanol, and dried in vacuo at ambient temperature for 24 hours to give 1-chloro- 4-(dimethylamino) butane hydrochloride as a white solid (115 g), m.p. 100°–105° C.

A stirred mixture of 1-chloro-4-(dimethylamino)-butane hydrochloride (115 g), thiourea (51.9 g) and ethanol (500 ml) was heated under reflux for 24 hours then allowed to stand at 4° C. for 24 hours. The resulting solid was collected by filtration, washed with ether, and dried in vacuo at ambient temperature for 24 hours to give S-[4-(dimethylamino)butyl]isothiourea dihydrochloride as an off-white solid (140 g), m.p. 179°–182° C.

A solution of sodium hydroxide (16.4 g) in water (16.5 ml) was added dropwise under nitrogen at 0° C. to a stirred solution of S-[4-(dimethylamino)butyl]-isothiourea dihydrochloride (51 g) in water (60 ml), then the mixture was heated at 95° C. for 2 hours and allowed to cool to ambient temperature. Water (100 ml) was added, and the product was extracted into ether (50 ml), dichloromethane (3×50 ml), and ether (2×50 ml). The combined organic solutions were dried over magnesium sulphate, then the solvents were removed in vacuo. The residue was dissolved in ether and the solution was saturated with hydrogen chloride. The resulting solid was collected by filtration and dried in vacuo at ambient temperature to give 4-(dimethylamino)butanethiol hydrochloride as a white solid (21 g) which was used without further purification.

A solution of sodium ethoxide [prepared from sodium (1.6 g) and ethanol (175 ml)] was added at ambient temperature under nitrogen to a stirred suspension of 4-(dimethylamino)butanethiol hydrochloride (5.5 g) in ethanol (75 ml) and the mixture was stirred at ambient temperature for 1 hour. A solution of 2-bromo-1-[1-( 3,4-dichlorophenyl)cyclobutyl]ethanone (11 g,prepared in a similar manner to that described in Example 1) in ethanol (40 ml) was added, and the mixture was stirred at ambient temperature for 48 hours. The solvent was removed in vacuo, and the residue was diluted with water (200 ml). The product was extracted into dichloromethane (4×90 ml) then the combined extracts were dried over sodium sulphate, and the solvent removed in vacuo. The residual oil was purified via column chromatography over silica using a 9:1 mixture of toluene and triethylamine as eluant. Appropriate fractions were combined, and the solvents were removed in vacuo. The residue was dissolved in ether, and the solution was saturated with hydrogen chloride. The resulting solid was collected by filtration, washed with ether, dried in vacuo over phosphorus pentoxide for 24 hours, and recrystallised from a 4:1 mixture of ethyl acetate and ethanol. The resulting solid was collected by filtration, washed with ethyl acetate, and dried. in vacuo at ambient temperature over phosphorus pentoxide for 48 hours to give 1-[1-(3,4-dichlorophenyl)cyclobutyl]-2-[4-(dimethylamino)-butylthio]ethanone hydrochloride as a white solid (5.6 g), m.p. 129°–130° C.

EXAMPLE 14

3-(Dipropylamino)propanol (32.9 g) was added dropwise at 0° C. over 1.5 hours to stirred thionyl chloride (15.7 ml). When the addition was complete, the mixture was stirred at ambient temperature for 2 hours then poured into ethanol (250 ml). The stirred mixture was heated under reflux for 10 minutes, then the solvent was removed in vacuo to leave 1-chloro-3-(dipropylamino)-propane hydrochloride as an off-white solid (42 g) which was used without purification.

A stirred mixture of 1-chloro-3-(dipropylamino)-propane hydrochloride (42 g), thiourea (15.5 g) and ethanol (250 ml) was heated under reflux for 24 hours then allowed to cool to ambient temperature. Ethyl acetate was added until a faint opalescence was observed, then the mixture was stored at 4° C. for 24 hours. After this time it had deposited an oil which was isolated by decantation of the bulk of the solvent followed by removal of residual solvent in vacuo. The oil was triturated with ethanol, the solvent was removed by decantation, and the residue was dried in vacuo at ambient temperature for 24 hours to give a pale brown solid. The ethanol solution decanted from the oil was concentrated in vacuo, and the residue was triturated with ethanol as described above to give a second crop of pale brown solid. The ethanol solution remaining after isolation of the second crop was concentrated in vacuo and the residue was triturated with propan-2-ol to give a third crop of solid. The three crops were combined to give S-[3-(dipropylamino)propyl] isothiourea dihydrochloride as a pale brown solid (51 g), m.p 143°–145° C.

25M Aqueous sodium hydroxide solution (11 ml) was added dropwise at 0° C. under nitrogen to a stirred solution of S-[3-(dipropylamino)propyl]isothiourea dihydrochloride (40 g) in water (100 ml), then the mixture was stirred at 95° C. for 2 hours and allowed to cool to ambient temperature. The product was extracted into ether (4×70 ml), the extracts were dried over magnesium sulphate, and the solvent was removed in vacuo. The residue was dissolved in ether, and the solution was saturated with hydrogen chloride to give a small amount of white solid which was collected by filtration. The filtrate was concentrated in vacuo, and the residue was combined with the white solid and dissolved in ethanol. The solution was saturated with hydrogen chloride and the solvent was removed in vacuo to leave crude 3-(dipropylamino)propanethiol hydrochloride (18.3 g) as a colourless semisolid which was used without purification.

A solution of sodium ethoxide [prepared from sodium (1.6 g) and ethanol (175 ml)] was added at ambient temperature under nitrogen to a stirred suspension of the crude 3-(dipropylamino)propanethiol hydrochloride (7 g) in ethanol (75 ml), then the mixture was stirred at ambient temperature for 1 hour. A solution of 2-bromo-1-[1-(3,4-dichlorophenyl)cyclobutyl]ethanone (10.6 g, prepared in a similar manner to that described in Example 1) in ethanol (40 ml) was added, and the mixture was stirred at ambient temperature for 24 hours. The solvent was removed in vacuo, the residue was diluted with water (100 ml), and the product was extracted into dichloromethane (4×75 ml). The extracts were dried over sodium sulphate, the solvent was removed in vacuo, and the residue was purified via column chromatography over silica using a 19:1 mixture of toluene and triethylamine as eluant. Appropriate fractions were combined and the solvents were removed in vacuo to leave 1-[1-(3,4-dichlorophenyl)cyclobucyl]-2- [3-(dipropylamino)propylthio]ethanone as a pale yellow oil (5.5 g).

EXAMPLE 15

A solution of fumaric acid (0.65 g) in hot ethanol (20 ml) was added to a solution of 1-[1-(3,4-dichlorophenyl)cyclobutyl]-2-[3-(dimethylamino) propylthio]ethanone (2.1 g, prepared by basification of the hydrochloride salt obtained in a similar manner to that described in Example 7) in ether (10 ml) and the mixture was allowed to stand at 4° C. for 96 hours. No solid precipitated, so the solvents were removed in vacuo to leave a brown oil which was triturated with petroleum ether (b.p. 40°–60° C.). The resulting solid was collected by filtration, washed with ether, dried in vacuo at ambient temperature for 18 hours, and recrystallised from a 3:2 mixture of ethyl acetate and petroleum ether (b.p. 60°–80° C.). The resulting solid was collected by filtration, washed with petroleum ether (b.p. 60°–80° C.), and dried in vacuo at ambient temperature for 18 hours to give 1-[1-(3, 4-dichloro-phenyl)cyclobutyl]-2-[3-(dimethylamino) propylthio]ethanone fumarate as a white solid (1.1 g), m.p. 100°–103° C.

EXAMPLE 16

Sodium borohydride (3.2 g) was added in portions at 0° C. under nitrogen to a stirred solution of 1-[1-(3,4-dichlorophenyl)cyclobutyl]-2-[3-(dimethylamino)-propylthio]ethanone (16 g, prepared by basification of the hydrochloride salt obtained in a similar manner to that described in Example 7) in methanol (200 ml) then the mixture was stirred at ambient temperature for 7 days and diluted with water (350 ml). The product was extracted into dichloromethane (4×100 ml) and the extracts washed with water (100 ml) and saturated aqueous sodium chloride solution (100 ml), dried over sodium sulphate and the solvent removed in vacuo to leave a green oil. The oil was resolved via preparative scale chiral high performance liquid chromatography to give (−)-1-[1-(3,4-dichlorophenyl) cyclobutyl]-2-[3 -(dimethylamino)propylthio]ethanol as an oil (3.5 g), $[\alpha]^{rt}_{D}=-8.615°$ (C=1;ethanol) and (+)-1-[1-(3 4-dichlorophenyl)cyclobutyl]-2-[3-(dimethylamino) propylthio]ethanol as an oil (3.4 g), $[\alpha]^{rt}_{D}=+9.740°$ (C=1; ethanol).

A solution of citric acid (1.77 g) in hot ethanol (10 ml) was added to a solution of (−) -1-[1-(3,4-dichlorophenyl) cyclobutyl]-2-[3-(dimethylamino)-propylthio]ethanol (3.42 g) in ether (30 ml), and the mixture was stored at 4° C. for 18 hours. The resulting solid was collected by filtration, washed with ether and dried in vacuo at ambient temperature for 24 hours, to give (−)-1-[1-(3,4-dichlorophenyl) cyclobutyl]-2-[3-(dimethylamino)propylthio]ethanol citrate as a white solid (3.9 g) , m.p. 109°–115° C., $[\alpha]^{rt}_{D}=-10.17°$ (C=1; methanol) .

EXAMPLE 17

A solution of citric acid (1.73 g) in hot ethanol (10 ml) was added to a solution of (+)-1-[1-(3,4-dichlorophenyl) cyclobutyl]-2-[3-(dimethylamino) propylthio]ethanol (3.29 g, preparation described in Example 16) in ether (30 ml) and the mixture was stored at 4° C. for 18 hours. The resulting solid was collected by filtration, washed with ether and dried in vacuo at ambient temperature for 24 hours, to give (+)-1-[1-(3,4-dichlorophenyl)cyclobutyl]-2-[3-(dimethylamino)-propylthio]ethanol citrate as a white solid (3.8 g) , m.p. 109°–115° C., $[\alpha]^{rt}_D$=+10.88° (C=1; methanol).

EXAMPLE 18

A stirred mixture of 1-chloro-3-(dimethylamino) propane hydrochloride (305.7 g), thiourea (150 g) and ethanol (1530 ml) was heated under reflux for 24 hours then cooled to ambient temperature. Ethyl acetate was added until a faint opalescence was observed, then the mixture was stored at 4° C. for 72 hours. The resulting solid was collected by filtration, washed with ethyl acetate, and dried in vacuo at 40° C. to give S-[3-(dimethylamino)propyl]isothiourea dihydrochloride as a white solid (403 g), m.p. 155°–157° C.

A solution of sodium hydroxide (250 g) in water (250 ml) was added at <25° C. over 10 minutes to a stirred solution of S-[3-(dimethylamino)propyl]isothiourea dihydrochloride (731 g; prepared in a similar manner to that described above) in water (880 ml), then the mixture was stirred at 95° C. for 3 hours and cooled to 10° C. The product was extracted into dichloromethane (4×500ml), the extracts were combined, and the solvent was removed in vacuo. The residue was disolved in ether (1l), the solution was decanted from a white solid residue, and the solvent was removed in vacuo to leave a colourless oil (362.7 g). The oil was added dropwise over 20 minutes at <15° C. to stirred 5M hydrochloric acid (650 ml), then the mixture was concentrated in vacuo at 70° C. to give a white solid. The solid was diluted with propan-2-ol (1l) and the solvent was removed in vacuo, then the residue was diluted with toluene (1l) and the solvent was removed in vacuo. The residue was triturated with ether (1l) and the resulting solid was collected by filtration, washed with ether, and dried in vacuo at 40° C. for 3 days and at ambient temperature over phosphorus pentoxide for 5 days to give 3-(dimethylamino)propanethiol hydrochloride as a white solid (405.9 g), m.p. 81°–84° C.

A solution of 1-(3,4-dichlorophenyl) cyclobutanecarbonitrile (163.6 g) in ether (130 ml) was added dropwise over 0.5 hours at ambient temperature under nitrogen to stirred methylmagnesium iodide (3M solution in ether; 300 ml), then the mixture was heated under reflux for 1 hour, diluted with ether (100 ml), heated under reflux for a further 2.5 hours, then stirred at ambient temperature for 18 hours. The resulting solid was collected by filtration, washed well with ether, and added in portions at <20° C. to a stirred mixture of concentrated hydrochloric acid (410 ml) and water (650 ml). The mixture was heated at 95° C. for 0.5 hours with occasional stirring then cooled to ambient temperature. The product was extracted into dichloromethane (3×200 ml), the combined extracts were dried over magnesium sulphate, and the solvent removed in vacuo to leave 1-[1-(3,4-dichlorophenyl)-cyclobutyl]ethanone as a dark red oil (172.7 g) which was used without purification.

A solution of bromine (96 ml) in chloroform (427 ml) was added dropwise at 10°–15° C. over 1.5 hours to a stirred solution of 1-[1-(3,4-dichlorophenyl)cyclobutyl]ethanone (477.2 g; prepared in a similar manner to that described above) in a mixture of methanol (643 ml) and chloroform (107 ml). After the addition was complete, the mixture was stirred at ambient temperature for 3 hours, then poured into ice-water (2l). The aqueous layer was separated and washed with dichloromethane (3×500 ml), then the combined organic solutions were washed with saturated aqueous sodium hydrogencarbonate solution (2×400 ml) and water (500 ml), dried over calcium chloride, and the, solvents were removed in vacuo to leave 2-bromo-1-[1-(3,4-dichlorophenyl)cyclobutyl]ethanone as an orange oil (593.5 g) which was used without purification.

A solution of 3-(dimethylamino)propanethiol (235.6 g; prepared by basification of the hydrochloride salt) in ethanol (1l) was added dropwise at ambient temperature to a stirred solution of sodium ethoxide [prepared from sodium (50 g) and ethanol (2l)], then the mixture was stirred at ambient temperature for 1 hour. A solution of 2-bromo-1-[1-(3,4-dichlorophenyl)-cyclobutyl]ethanone (817.4 g; prepared in a similar manner to that described above) in ethanol (1.5l) was added and the mixture was stirred at ambient temperature for 18 hours. The solvent was removed in vacuo, and the solid residue was diluted with water (2l). The product was extracted into dichloromethane (3×500 ml), the combined extracts were dried over magnesium sulphate, and the solvent was removed in vacuo. The residue was disolved in ether, the solution was decanted from an insoluble gum, and the solvent was removed in vacuo to leave an orange oil (713 g). The oil was dissolved in petroleum ether (b.p. 60°–80° C.) (3.5l), charcoal and magnesium sulphate were added, the mixture was filtered (celite), and the solvent was removed in vacuo to leave a pale orange oil (713 g). The oil was added at <20° C. to a stirred mixture of concentrated hydrochloric acid (255 ml) and water (1750 ml) then the mixture was concentrated in vacuo at 50° C. The residue was repeatedly diluted with toluene and concentrated in vacuo until all of the water had been removed, then the residue was triturated with ether (2.5l). The ether was removedby decantation, and the residue was dissolved in ethyl acetate (2.5l). Ether (5l) was added, and the resulting solid was collected by filtration, washed with ether, suspended in ethyl acetate (2.5l), collected by filtration, washed with ethyl acetate, and dried in vacuo at 50° C. to give crude 1-[1-(3,4-dichlorophenyl)cyclobutyl]-2-[3-(dimethylamino)-propylthio]ethanone hydrochloride as a cream solid (425 g). Repetition of this experiment on approximately ½ scale gave further crude product as a cream solid (313 g).

The two crops of impure solid were combined, dissolved in water (2.5l), and basified to pH9 by addition of solid sodium carbonate. The free base was extracted into dichloromethane (3×500 ml) and the solvent was removed in vacuo. The resulting gum was partitioned between water and ethyl acetate; an emulsion formed, so the mixture was filtered (Celite), then the organic layer was separated, dried over sodium sulphate and the solvent was removed in vacuo to leave a brown oil (638 g). The oil was purified in portions (50 g) by filtration through silica using a 9:1 mixture of dichloromethane and methanol as eluant. Appropriate fractions were combined and the solvents were removed in vacuo to give a pale orange oil (484.3 g). The oil was added at <20° C. to a stirred mixture of concentrated hydrochloric acid (173 ml) and water (415 ml), and the resulting mixture was concentrated in vacuo. The residue was dried by repeated dilution with toluene and removal of the solvent in vacuo, then the resulting gum was dissolved in ethyl acetate (500 ml) and diluted with ether (2.5l). The resulting solid was collected by filtration, washed with ether and dried in vacuo at 45° C. to give 1-[1-(3,4-dichlorophenyl)cyclobutyl]-2-[3-(dimethylamino)propylthio]ethanone hydrochloride as a cream solid (507.1 g).

1-[1-(3,4-Dichlorophenyl)cyclobutyl]-2-[3-(dimethylamino)propylthio]ethanone hydrochloride (480 g) was suspended in an excess of saturated aqueous sodium hydrogencarbonate solution, the mixture was stirred at ambient temperature for 0.5 hours, then the free base was extracted into dichloromethane. The extracts were dried over sodium sulphate and the solvent was removed in vacuo to leave a brown oil (415 g). The oil was dissolved in ether (1700 ml) and added to a solution of citric acid (210 g) in hot ethanol (3200 ml), then the mixture was allowed to cool to ambient temperature and was stored at 4° C. for 48 hours whereupon it deposited a pale brown solid. The supernatent liquor was removed by decantation, the residue was diluted with ethanol (300 ml), and the mixture was warmed gently to loosen the crystalline mass. The product was collected by filtration, washed with ether, dried in vacuo, and recrystalised from ethanol. The resulting solid was collected by filtration, washed with ethanol, and dried in vacuo at 50° C. for 4 hours to give 1-[1-(3,4-dichlorophenyl)cyclobutyl]-2-[3-(dimethylamino) propylthio]ethanone citrate as a cream solid (410 g), m.p. 103°–105° C.

EXAMPLE 19

The mother liquors remaining after isolation of the product described in Example 10 were concentrated in vacuo and the residue was diluted with water and basified by the addition of 5M aqueous sodium hydroxide solution. The product was extracted into ether and the extracts were washed with water, dried over magnesium sulphate and the solvent removed in vacuo to leave 1-[1-(3,4-dichlorophenyl)cyclobutyl]-2-[3-(dimethylamino)-2-methylpropylthio]ethanone as a pale yellow oil. A sample (4 g) of this oil was dissolved in methanol (40 ml) and sodium borohydride (0.8 g) was added in portions under nitrogen at 0° C. The mixture was stirred at ambient temperature for 7 days then diluted with water (120 ml). The product was extracted into dichloromethane (4×50 ml) then the combined extracts were washed with water (50 ml) and saturated aqueous sodium chloride solution (50 ml), dried over sodium sulphate and the solvent removed in vacuo to give a colourless oil (4.2 g).

The oil was dissolved in ether and the solution saturated with hydrogen chloride to give a solid which was collected by filtration, washed with ether and dried in vacuo over phosphorus pentoxide for 72 hours. The resulting white solid was hygroscopic, so it was dissolved in water and basified by the addition of saturated aqueous sodium hydrogencarbonate solution. The product was extracted into dichloromethane (3×50 ml) and the combined extracts were washed with water, dried over sodium sulphate and the solvent removed in vacuo to leave 1-[1-(3,4-dichlorophenyl)cyclobutyl]-2-[3-(dimethylamino)-2-methylpropylthio]ethanol as a pale green oil (3 g).

EXAMPLE 20

1,4-Dibromobutane (106 ml) was added dropwise over 1 hour at 70°–80° C. under nitrogen to a stirred mixture of 3,4-dichlorophenylacetonitrile (150 g) , benzyltriethylammonium chloride (2 g) and 50% aqueous sodium hydroxide solution (300 ml). When the addition was complete the mixture was stirred at 70°–80° C. for 2 hours, then cooled to ambient temperature. Ether (400 ml) and water (200 ml) were added and the layers were separated. The aqueous layer was washed with ether (2×200 ml), then the combined organic solutions were dried over magnesium sulphate and the solvent removed in vacuo. The residue was distilled to give 1-(3,4-dichlorophenyl)cyclopentanecarbonitrile as a pale yellow oil (135 g), b.p. 132°–140° C./0.4 mbar.

Methylmagnesium iodide (3M solution in ether; 100 ml) was added dropwise at 0° C. under nitrogen to a stirred solution of 1-(3,4-dichlorophenyl) cyclopentanecarbonitrile (48 g) in ether (100 ml), then the mixture was stirred at ambient temperature for 24 hours. The resulting solid was collected by filtration, washed with ether, and added in portions to an ice-cold mixture of water (200 ml) and concentrated hydrochloric acid (125 ml). The mixture was heated at 95° C. for 1 hour, then allowed to cool to ambient temperature. The product was extracted into ether (5×100 ml), and the combined extracts were washed with water (2×100 ml), dried over magnesium sulphate, and the solvent removed in vacuo. The residue was distilled to give 1-[1-(3,4-dichlorophenyl)cyclopentyl]ethanone as a pale yellow oil (31.9 g), b.p. 124°–128° C./0.5 mbar.

A solution of bromine (6.1 ml) in dichloromethane (50 ml) was added dropwise over 3 hours at 10°–15° C. under nitrogen to a stirred solution of 1-[1-(3,4-dichlorophenyl)cyclopentyl]ethanone (31.9 g) in a mixture of methanol (60 ml) and dichloromethane (10 ml), then the mixture was stirred at ambient temperature for 2.5 hours and poured into an excess of ice-water. The aqueous layer was separated and washed with dichloromethane 3×100 ml), then the combined organic solutions were washed with saturated aqueous sodium hydrogencarbonate solution (2×100 ml) and water (100 ml), dried over calcium chloride, and the solvent removed in vacuo. The residue was distilled in vacuo, and the fraction of b.p. >174° C./1.3 mbar was collected and redistilled. Material of b.p. >182° C./2.6 mbar in this second distillation was collected and redistilled to give 2-bromo-1-[1-(3,4-dichlorophenyl)cyclopentyl]ethanone as a pale yellow oil (11.8 g), b.p. 156°–162° C./0.4 mbar.

A solution of sodium ethoxide [prepared from sodium (1.4 g) and ethanol (175 ml)]was added at ambient temperature under nitrogen to a stirred suspension of 3-(dimethylamino)propanethiol hydrochloride (4.5 g, prepared in a similar manner to that described in Example 7) in ethanol (75 ml), then the mixture was stirred at ambient temperature for 1 hour. A solution of 2-bromo-1-[1-(3,4-dichlorophenyl)cyclopentyl]ethanone (10.5 g) in ethanol (40 ml) was added, and the mixture was stirred at ambient temperature for 24 hours. The solvent was removed in vacuo, the residue was diluted with water (100 ml), and the product was extracted into dichloromethane (4×75 ml). The extracts were dried over sodium sulphate, the solvent was removed in vacuo, and the residue was purified via column chromatography over silica using a 19:1 mixture of toluene and triethylamine as eluant. Appropriate fractions were combined and the solvents removed in vacuo to leave a pale brown oil (7 g). The oil was dissolved in ether, the solution was saturated with hydrogen chloride, and the solvent was removed in vacuo. The residue was triturated with ether, and the resulting solid was collected by filtration, washed with ether, and dried in vacuo at ambient temperature over phosphorus pentoxide for 48 hours to give 1-[1-(3,4-dichlorophenyl) cyclopentyl]-2-[3-(dimethylamino) propylthio]ethanone hydrochloride as a white solid (5.6 g), m.p. 77°–80° C.

EXAMPLE 21

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets

Tablets are prepared from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

Suppositories

In the preparation of suppositories, 100 parts by weight of active compound is incorporated in 1300 parts by weight of triglyceride suppository base and the mixture formed into suppositories each containing a therapeutically effective amount of active ingredient.

We claim:

1. A compound of the formula I

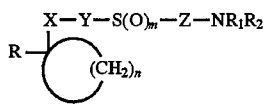                I and pharmaceutically acceptable salts thereof in which m is 0, 1 or 2;

n is 2, 3, 4 or 5;

X is carbonyl or a group of formula II

                II in which $R_5$ is H or an alkyl group containing 1 to 4 carbon atoms;

Y is an alkylene chain containing 1 or 2 carbon atoms optionally substituted by one or more alkyl groups containing 1 to 3 carbon atoms;

Z is an alkylene chain containing 2 to 5 carbon atoms optionally substituted by one or more alkyl groups containing 1 to 3 carbon atoms;

R is phenyl optionally substituted by one or more halo substituents or R is naphthyl; and $R_1$ and $R_2$, which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl.

2. A compound of the formula I as defined in claim 1 in which m is 0,1 or 2 and n is 3 or 4.

3. A compound of the formula I as defined in claim 1 in which X is carbonyl or a group of formula II in which $R_5$ is H.

4. A compound of the formula I as defined in claim 1 in which Y is methylene.

5. A compound of the formula I as defined in claim 1 in which Z is an alkylene chain containing 2,3 or 4 carbon atoms optionally substituted by one or more alkyl groups containing 1 to 3 carbon atoms.

6. A compound of the formula I as defined in claim 1 in which Z is an alkylene chain containing 2,3 or 4 carbon atoms optionally substituted by one or more methyl groups.

7. A compound of the formula I as defined in claim 1 in which R is phenyl substituted by one or two chloro substituents or R is naphthyl.

8. A compound of the formula I as defined in claim 1 in which R is 3-chlorophenyl, 3,4-dichlorophenyl or 2-naphthyl.

9. A compound of the formula I as declined in claim 1 in which $R_1$ is an alkyl group containing 1 to 3 carbon atoms or is benzyl, and $R_2$ is an alkyl group containing 1 to 3 carbon atoms.

10. A compound of the formula I as defined in claim 1 in which $R_1$ and $R_2$ are both methyl or ethyl or $R_1$ is benzyl and $R_2$ is methyl.

11. A compound of the formula III

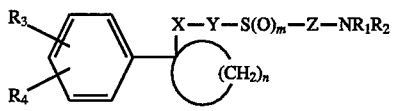                III and pharmaceutically acceptable salts thereof in which m is 0, 1 or 2;

n is 2, 3, 4 or 5;

X is carbonyl or a group of formula II

                II in which $R_5$ is H or an alkyl group containing 1 to 4 carbon atoms;

Y is an alkylene chain containing 1 or 2 carbon atoms optionally substituted by one or more alkyl groups containing 1 to 3 carbon atoms;

Z is an alkylene chain containing 2 to 5 carbon atoms optionally substituted by one or more alkyl groups containing 1 to 3 carbon atoms;

$R_1$ and $R_2$, which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl;

and $R_3$ is halo, and $R_4$ is H or halo, or $R_3$ and $R_4$ together with the carbon atoms to which they are attached form a fused benzene ring.

12. A compound of the formula III as defined in claim 11 in which $R_3$ is chloro and $R_4$ is H, $R_3$ and $R_4$ are both chloro or $R_3$ and $R_4$ together with the carbon atoms to which they are attached form a fused benzene ring.

13. A compound of the formula III as defined in claim 11 in which $R_3$ is chloro situated in the 3-substitution position on the phenyl ring and $R_4$ is H, $R_3$ and $R_4$ are both chloro and are situated in the 3- and 4- substitution positions on the phenyl ring respectively, or $R_3$ and $R_4$ together with the phenyl ring to which they are attached form a 2-naphthyl group.

14. A compound of the formula I as defined in claim 1 which is:

1-[1-(3,4-dichlorophenyl)cyclobutyl]-2-[2-(dimethylamino) ethylthio]ethanone;

1-[1-(3,4-dichlorophenyl)cyclobutyl]-2-[2-(dimethylamino) ethylsulphinyl]ethanone;

1-[1-(3,4-dichlorophenyl)cyclobutyl]-2-[2-(dimethylamino) ethylsulphonyl]ethanone;

1-[1-(3,4-dichlorophenyl)cyclobutyl]-2-[2-(diethylamino) ethylthio]ethanone;

2-[2-(N-benzyl -N-methylamino)ethylthio]-1-[1-(3,4-dichlorophenyl)cyclobutyl]ethanone;

1-[1-(3,4-dichlorophenyl)cyclobutyl]-2-[2-(dimethylamino) ethylthio]ethanol;

1-[1-(3,4-dichlorophenyl)cyclobutyl]-2-[3-(dimethylamino) propylthio]ethanone;

1-[1-(3,4-dichlorophenyl)cyclobutyl]-2-[3-(dimethylamino) propylsulphonyl]ethanone;

1-[1-(3,4-dichlorophenyl)cyclobutyl]-2-[3-(dimethylamino) propylthio]ethanol;

1-[1-(3,4-dichlorophenyl)cyclobutyl]-2-[3-(dimethylamino) -2-methylpropylthio]ethanone;

2-[2-(dimethylamino)ethylthio]-1-[1-(2-naphthyl) cyclobutyl]ethanone;

1-[1-(3-chlorophenyl)cyclobutyl]-2-[3-(dimethylamino) propylthio]ethanone;

1-[1-(3,4-dichlorophenyl)cyclobutyl]-2-[4-(dimethylamino) butylthio]ethanone;

1-[1-(3,4-dichlorophenyl)cyclobutyl]-2-[3-(dipropylamino) propylthio]ethanone;

1-[1-(3,4-dichlorophenyl)cyclobutyl]-2-[3-(dimethylamino) -2-methylpropylthio]ethanol;

1-[1-(3,4-dichlorophenyl)cyclopentyl]-2-[3-(dimethylamino)propylthio]ethanone;

and pharmaceutically acceptable salts thereof in the form of individual enantiomers, racemates, or other mixtures of enantiomers.

15. A pharmaceutical composition comprising a therapeutically effective amount of a compound formula I as defined in claim 1, together with a pharmaceutically acceptable diluent or carrier.

16. A method of neuroprotection or of treating depression, anxiety, Parkinson's disease, obesity, cognitive disorders, seizures, and neurological disorders which comprises the administration of a therapeutically effective amount of a compound of formula I as defined in claim 1 to a patient in need thereof.

17. A method as defined in claim 16 for treating depression.

18. A method as defined in claim 16 for treating anxiety.

19. A method as defined in claim 16 for treating Parkinson's Disease.

20. A process for the preparation of a compound of the formula I

and pharmaceutically acceptable salts thereof in which m is 0, 1 or 2;

n is 2, 3, 4 or 5;

x is carbonyl;

Y is an alkylene chain containing 1 or 2 carbon atoms optionally substituted by one or more alkyl groups containing 1 to 3 carbon atoms;

Z is an alkylene chain containing 2 to 5 carbon atoms optionally substituted by one or more alkyl groups containing 1 to 3 carbon atoms;

R is phenyl optionally substituted by one or more halo substituents or R is naphthyl; and $R_1$ and $R_2$, which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl;

said process comprising reaction of a compound of formula IV

in which G is a leaving group, with a compound of formula V

or a salt thereof in the presence of a base.

* * * * *

UNITED STATES PATENT AND TRADEMARK OFFICE
CERTIFICATE OF CORRECTION

PATENT NO.: 5,652,271

DATED: July 29, 1997

INVENTOR(S): HARRIS et al.

It is certified that error appears in the above-identified patent and that said Letters Patent is hereby corrected as shown below:

Column 24, claim 9, line 18, delete "declined" and substitute --defined--.

Signed and Sealed this

Seventh Day of October, 1997

Attest:

BRUCE LEHMAN

Attesting Officer

Commissioner of Patents and Trademarks